(12) United States Patent
Burch et al.

(10) Patent No.: US 7,255,677 B2
(45) Date of Patent: Aug. 14, 2007

(54) DETECTION, DIAGNOSIS, AND MONITORING OF A MEDICAL CONDITION OR DISEASE WITH ARTIFICIAL OLFACTOMETRY

(75) Inventors: Timothy E. Burch, San Gabriel, CA (US); C. William Hanson, III, Radnor, PA (US); Erica R. Thaler, Merion Station, PA (US)

(73) Assignees: Smiths Detection Inc., Pasadena, CA (US); Trustees of University of Pennsylvania, Philadelphia, PA (US)

( * ) Notice: Subject to any disclaimer, the term of this patent is extended or adjusted under 35 U.S.C. 154(b) by 357 days.

(21) Appl. No.: 10/382,360

(22) Filed: Mar. 4, 2003

(65) Prior Publication Data

US 2004/0006257 A1 Jan. 8, 2004

Related U.S. Application Data

(60) Provisional application No. 60/361,941, filed on Mar. 4, 2002.

(51) Int. Cl.
*A61B 5/00* (2006.01)

(52) U.S. Cl. ..................... 600/300; 600/532

(58) Field of Classification Search ............. 600/300, 600/301, 529–538; 128/898, 920; 422/84; 73/23.3
See application file for complete search history.

(56) References Cited

U.S. PATENT DOCUMENTS

| | | | |
|---|---|---|---|
| 3,897,679 A | 8/1975 | Guild | |
| 4,381,922 A | 5/1983 | Frey et al. | |
| 4,670,405 A | 6/1987 | Stetter et al. | |
| 4,718,268 A | 1/1988 | Reid et al. | |
| 4,749,553 A | 6/1988 | Lopez et al. | |
| 4,759,210 A | 7/1988 | Wholtjen | |
| 4,818,348 A | 4/1989 | Stetter | |
| 5,025,653 A | 6/1991 | Schuldt | |
| 5,239,483 A | 8/1993 | Weir | |
| 5,248,617 A | 9/1993 | De Haan | |
| 5,265,463 A | 11/1993 | Loebig | |
| 5,269,169 A | 12/1993 | Trenkle et al. | |
| 5,325,705 A | 7/1994 | Tom | |

(Continued)

FOREIGN PATENT DOCUMENTS

WO WO95/33848 A1 12/1995

(Continued)

OTHER PUBLICATIONS

Chandiok et al., *J. Clin. Path.*, 50(9):790-791 (1997).

(Continued)

*Primary Examiner*—Max F. Hindenburg
*Assistant Examiner*—Michael C. Astorino
(74) *Attorney, Agent, or Firm*—Foley & Lardner LLP

(57) ABSTRACT

Methods and devices for rapid diagnosis and monitoring a patient for disease or effectiveness of treatment in real time. In preferred embodiments, the methods and devices comprise contacting an array of sensors with a sample from a mammal suspected of having a disease to generate a sensor array profile, measuring a clinical diagnostic marker for the suspected disease, and then developing a diagnosis using the sensor array profile in combination with the clinical diagnostic marker.

8 Claims, 8 Drawing Sheets

U.S. PATENT DOCUMENTS

| | | | |
|---|---|---|---|
| 5,369,978 | A | 12/1994 | Mookherjee et al. |
| 5,469,369 | A | 11/1995 | Rose-Pehrsson et al. |
| 5,479,815 | A | 1/1996 | White et al. |
| 5,522,918 | A | 6/1996 | Shiramizu |
| 5,546,931 | A | 8/1996 | Rusz |
| 5,571,401 | A | 11/1996 | Lewis et al. |
| 5,585,575 | A | 12/1996 | Corrigan et al. |
| 5,621,162 | A | 4/1997 | Yun et al. |
| 5,635,626 | A | 6/1997 | Hammond et al. |
| 5,739,412 | A | 4/1998 | Stock et al. |
| 5,807,701 | A | 9/1998 | Payne et al. |
| 5,814,474 | A | 9/1998 | Berndt |
| 5,814,524 | A | 9/1998 | Walt et al. |
| 5,882,497 | A | 3/1999 | Persaud et al. |
| 5,891,398 | A | 4/1999 | Lewis et al. |
| 5,965,803 | A | 10/1999 | Chinn, Jr. et al. |
| 6,033,601 | A | 3/2000 | Persaud et al. |
| 6,180,064 | B1 | 1/2001 | Persaud et al. |
| 6,190,858 | B1 | 2/2001 | Persaud et al. |
| 6,192,351 | B1 | 2/2001 | Persaud |
| 6,206,829 | B1 * | 3/2001 | Iliff .................... 600/300 |
| 6,234,006 | B1 * | 5/2001 | Sunshine et al. ........... 600/532 |
| 6,236,951 | B1 | 5/2001 | Payne et al. |
| 6,244,096 | B1 | 6/2001 | Lewis et al. |
| 6,319,724 | B1 | 11/2001 | Lewis et al. |
| 6,376,232 | B1 | 4/2002 | Payne et al. |
| 6,431,016 | B1 | 8/2002 | Payne et al. |
| 6,461,306 | B1 * | 10/2002 | Hanson et al. ............. 600/532 |
| RE38,186 | E | 7/2003 | Payne et al. |
| 6,620,107 | B2 | 9/2003 | Payne et al. |
| 6,627,412 | B1 | 9/2003 | Manning et al. |
| 6,655,010 | B1 | 12/2003 | Hatfield et al. |
| 7,052,468 | B2 * | 5/2006 | Melker et al. ............. 600/532 |

FOREIGN PATENT DOCUMENTS

| | | |
|---|---|---|
| WO | WO96/07901 A1 | 3/1996 |
| WO | WO97/08337 A1 | 3/1997 |
| WO | WO98/29563 A1 | 7/1998 |
| WO | WO98/36272 A1 | 8/1998 |
| WO | WO98/39409 A1 | 9/1998 |
| WO | WO98/39470 A1 | 9/1998 |
| WO | WO99/09407 A1 | 2/1999 |
| WO | WO99/09408 A1 | 2/1999 |
| WO | WO99/65386 A1 | 12/1999 |

OTHER PUBLICATIONS

Craven et al., "Bacteria Detection and Classification Using Artificial Neural Networks in Conjunction with an Electronic Nose," Proceedings of the 2nd International Conference on Neural Networks and Expert Systems in Medicine and Healthcare, pp. 226-234 (1996).

Greenfield, "AromaScan sniffs out medical applications," *Clinica*, pp. 20-21, May 23, 1994.

Parry et al., *J. Wound Care*, 4(9):404-406 (1995).

* cited by examiner

DETECTION, DIAGNOSIS, AND MONITORING OF A MEDICAL CONDITION OR DISEASE WITH ARTIFICIAL OLFACTOMETRY

CROSS-REFERENCES TO RELATED APPLICATIONS

This application claims priority to U.S. Patent Application No. 60/361,941, filed Mar. 4, 2002, the disclosure of which is hereby incorporated by reference in its entirety for all purposes.

BACKGROUND OF THE INVENTION

I. Introduction

The sense of smell has been used in medicine for thousands of years, from early Greek and Chinese practitioners to modern clinicians (see, Hayden et al., Post grad. Med., 67:110-118 (1980); Kerr et al., Trends in Microbiology, 9:59 (2001); Saini et al., Biologist, 48:229-233 (2001)). However, smell has not been utilized for routine diagnostic purposes, perhaps due to the subjective nature of human odor recognition as well as the possibly complex biological origins of chemical signatures that constitute a "medical odor."

Recent advances in odor sensing technology, signal processing and diagnostic algorithms have created chemical sensing and identification devices called "electronic noses" (see, Kerr et al., Trends in Microbiology, 9:59 (2001)). The electronic nose has been used for several years in a wide variety of industrial and commercial applications. In the laboratory, these devices have been shown to differentiate bacterial cultures (see, Kerr et al., Sniffing out Infection, Trends in Microbiology, 9, 59, (2001); Saini et al., Biologist, 48, 229-233, (2001).

Multiple groups have used electronic nose technology for recognition of disease in vivo (see, Martini A et al., Critical Reviews in Biomedical Engineering, 28:481-485 (2000)). In veterinary science, an electronic nose device was used to identify dietary ketosis in dairy cattle from breath measurement. In medicine, applications have been reported that range from the detection of pneumonia to differentiation of serum from cerebrospinal fluid (see, Dr. E. Thaler, Univ. Penn. Hospital, personal communication (2001); Hanson et al., The use of a novel 'electronic nose' to diagnose the presence of intrapulmonary infection. Anesthesiology, 87, A269 (1997). Recently, the potential use of the electronic nose as a screening tool was demonstrated for bacterial vaginosis and urinary tract infection (see, Chandiok, et al., Screening for Bacteria Vaginosis: A Novel Application of Artificial Nose Technology, J. Clin. Pathol. 50:790-791 (1997); Aathithan et al. Diagnosis of Bacteriuria by Detection of Volatile Organic Compounds in Urine Using an Automated Headspace Analyzer with Multiple Conducting Polymer Sensors, J. Clin. Microbiol. 39:2590-2593 (2001).

As described above, electronic noses are currently being used to diagnose disease by identification of marker gases from particular microorganisms. However, it would be useful to diagnose a disease or condition based on the presence of a collection of odorants, ("smellprint") or a volatile chemical signature, rather than one specific odorant. Such a method would allow for rapid and accurate detection of any disease associated with a particular "smellprint." In particular, the method would be useful for screening for diseases with complex presentations and diseases where diagnosis is slow and problematic, such as ventilator-associated pneumonia and sinusitis. The method would also be useful for monitoring diseases and conditions in real time.

II. Medical Applications

A. Ventilator-Associated Pneumonia

Nosocomial pneumonia (NP) is the second most common nosocomial infection in the U.S. with an incidence of 5-10 per 1000 hospital admissions. It has the highest morbidity and mortality of the nosocomial infections tracked by the Centers for Disease Control, and the diagnosis is associated with the prolongation of hospital stays by 7-9 days. The crude mortality rate for nosocomial pneumonia (NP) may be as high as 70%.

The incidence of NP increases by 6-20 fold in mechanically ventilated patients. Ventilator associated pneumonia (VAP) is defined as a parenchymal lung infection occurring greater than 48 hours after initiation of mechanical ventilation. It occurs in 10-25% of patients intubated for longer than 48 hours, and it is the most common associated infection in intensive care patients according to some studies (see, C. W. Hanson, Pneumonia. "In: M. J. Murray et al (eds.), Critical Care Medicine: Perioperative Management, 2nd Ed. Lippincott, Williams & Wilkins, Philadelphia" (2002)). VAP has an associated mortality rate of 25-70%. The risk of VAP increases with increased duration of mechanical ventilation.

Survival rates improve with appropriate treatment, but the diagnosis of pneumonia in the ICU patient is difficult and most tests are invasive, requiring sampling devices of varying complexity to be inserted into the lungs. Signs and symptoms of infection in this population can have multiple causes. Radiographic evidence of pneumonia can be mimicked by other conditions. Culture results have a high rate of false-negatives after the administration of antibiotics. In addition, regardless of whether the patient is being treated with antibiotics, culture results are often mixed or inconclusive due to threshold criteria for pathogen identification. Further compounding the problem is the variability in threshold criteria between labs. Due to the difficulty of diagnosing bacterial pneumonia, the Clinical Pulmonary Infection Score (CPIS) has become an "accepted standard" (see, Pugin et al., American Review of Respiratory Disease, 143(5 Pt 1):1121-9 (1991)). The CPIS score is a cumulative score developed from several individual measures that include temperature, white cell count, secretion amount and character, pulmonary function (PaO2/FIO2 ratio), chest radiograph infiltrates and tracheal aspirate culture.

An electronic nose can aid in the rapid and accurate diagnosis and treatment of ventilator-associated pneumonia, potentially reducing morbidity and mortality in this population, as well as containing and reducing hospital costs incurred by testing and increased length of hospital stay.

B. Sinusitis

Acute and chronic sinusitis together make up the most commonly used ICD9 code in the United States, surpassing both hypertension and atherosclerosis. Sixty-six million adults, fully 35% of the adult U.S. population, report having sinusitis or sinus problems at least once during the previous 12 months (Dr. E. Thaler, "Univ. Penn. Hospital, personal communication" (2001)). Sinusitis is the most frequently reported chronic condition, affecting 14.1% of the U.S. population.

However, the diagnosis of sinusitis can be difficult to make, as it may be confused with various other nasal conditions. The best means of securing the diagnosis is by identification of bacterial pathogens upon culture of the involved sinuses. Studies have shown that 70% of acute sinusitis cases are caused by *Streptococcus pneumoniae* and *Haemophilus influenzae* in adults and children. Other species, including *Moraxella catarrhalis* and *Staphylococcus aureus*, are also significant contributors to acute sinusitis. The problem with this method of diagnosis is that it takes 48 hours to identify the bacteria on culture, and takes further time to determine antibiotic susceptibility. In addition, the presence of normal oralpharyngial flora may confound the results.

An electronic nose would assist physicians in determining which patients require further testing, i.e., microbiological culture, and which do not. Effective screening could reduce the number of negative samples sent for microbiological culture and the number of prescriptions for broad-spectrum antibiotics, thereby reducing the drug resistance of bacteria. Rapid identification of the predominant bacterial species responsible for sinus infection in patients would provide a guide for physicians in choosing antibiotics in real time, along the lines of the rapid strep test used for acute pharyngitis.

Thus it is clear that there is a need for methods and devices that diagnose disease or a condition by detecting a multiple-component "smellprint" associated with the disease or a condition. Such methods allow for rapid (within the hour) diagnosis of disease and monitoring of disease in real time. The present invention fulfills this and other needs.

BRIEF SUMMARY OF THE INVENTION

In one aspect, the present invention provides a method for rapidly detecting disease or a condition in a mammal. In the past, it has often been necessary to perform multiple, time-consuming tests in order to diagnose a disease or condition. Advantageously, the rapid diagnosis possible with this method can be used to refine the initial treatment plan, resulting in earlier and more accurate intervention, and to monitor the progress of treatment after administration.

The method comprises contacting an array of sensors with a sample from a mammal suspected of having a disease or condition to generate a sensor array response profile, measuring a clinical diagnostic marker for the disease or condition, and developing a diagnosis using the sensor array response profile in combination with a clinical diagnostic marker. The sensor array response profile can be generated prior to measuring the clinical diagnostic marker, concurrently with measuring the clinical diagnostic marker, subsequent to measuring the clinical marker, or in some combination thereof.

In certain embodiments, the method comprises analyzing the sensor array response profile to identify a marker gas in the sample. The marker gas can include, but is not limited to, alkanes, alkenes, alkynes, dienes, cyclic hydrocarbons, aliphatic hydrocarbons, acyclic hydrocarbons, amines, arenes, alcohols, ethers, ketones, aldehydes, carbonyls, carbanions, polynuclear aromatics, biomolecules, sugars, isoprenes, isoprenoids, VOC, VOA, indoles, skatoles, diamines, pyridines, picolines, sulfur compounds, halogenated compounds, organic acids, organic bases, fatty acids, and fixed gases including CO, $CO_2$, NO, $NO_2$, $NH_3$, $H_2S$, and COS. The marker gas can be an off-gas of a virus, a fungus, or a bacterium. It can also be an off-gas or gas resulting from a chemical change produced by the disease process or the immune system response to the disease or condition, or the response to therapeutic treatment. By way of example, the marker gas can include gases from microorganisms including, but not limited to, *Streptococcus pneumoniae, Streptococcus pyogenes, Staphylococcus aureus, Moraxella catarrhalis, Haemophilus influenzae, Prevotella intermedia, Fusobacterium nucleatum, Porphyromonas gingivalis, Porphyromonas endodontalis, Prevotella loescheii, Hemophilus parainfluenzae, Stomatococcus muci, Treponema denticola,* Veillonella species, *Peptostreptococcus anaerobius, Micros prevotii, Eubacterium limosum, Centipeda periodontii, Selemonad aremidis,* Eubacterium species, Bacteriodes species, *Fusobacterium periodonticum, Prevotella melaninogenica, Klebsiella pneumoniae, Enterobacter cloacae,* Citrobacter species, *Stomatococcus mucilaginus,* and *Pseudomonas aeruginosa.*

The clinical diagnostic marker used with the sensor array profile to develop a diagnosis can include, but is not limited to, Clinical Pulmonary Infection Score (CPIS), temperature, erythrocyte counts, leukocyte counts, secretion amount and character, radiography, respiratory function, microbiological culture, and other serological markers.

The sample can be the breath of a mammal, the breath condensate of a mammal, the saliva of a mammal, the blood of a mammal, mucous of a mammal, swabbings taken from a mammal, off gas from a mammalian secretion, or the urine of a mammal. In a preferred embodiment, the sample is the breath of a mammal. The breath of the mammal can be taken directly from a ventilator.

The disease or condition detected or monitored by methods of this invention can be a viral infection, a bacterial infection, or a fungal infection. In certain embodiments, the disease is a bacterial infection. The infection can be a lower respiratory tract infection like pneumonia (e.g., ventilator-associated pneumonia) or bronchitis. The disease can also be an upper respiratory tract infection like sinusitis, pharyngitis, or otitis media. In certain embodiments, the conditions detected or monitored by methods of this invention are not an infection.

The array of sensors can be in its own separate unit, embedded in ventilator tubing, embedded in the ventilator filter, or located in the fluid stream between the patient lungs and the ventilator pump. In certain embodiments the array of sensors is contained in a handheld device.

In another aspect, the present invention provides a method for determining whether a mammal has a disease or condition, the method comprising contacting an array of sensors with a sample from a mammal suspected of having a disease or condition to generate a first sensor array response profile and comparing the first sensor array response profile with a sensor array profile from a healthy mammal.

In yet another aspect, the present invention provides a method for determining the severity of a disease or condition in a mammal. The method comprises contacting an array of sensors with a sample from a mammal suspected of having a disease or condition to generate a first sensor array response profile, contacting an array of sensors with a sample from a mammal suspected of having a disease or condition to generate a second sensor array response profile and evaluating the difference between the first and second sensor array profiles.

In still yet another aspect, the present invention provides a method for monitoring a disease or condition in a mammal comprising contacting an array of sensors with a sample from a mammal having a disease or condition to generate a baseline sensor array response profile, measuring a clinical diagnostic marker for the disease or condition, determining the severity of the disease or condition using the sensor array response profile in combination with the clinical diagnostic marker, contacting an array of sensors with a sample from a mammal having a disease or condition for a second time to generate a second sensor array response profile, measuring the clinical diagnostic marker for the disease or condition for a second time, and determining the severity of the disease or condition using the first and second sensor array response profiles in combination with the first and second measurement of the clinical diagnostic marker.

DETAILED DESCRIPTION OF THE INVENTION

I. Definitions

Figure 1:
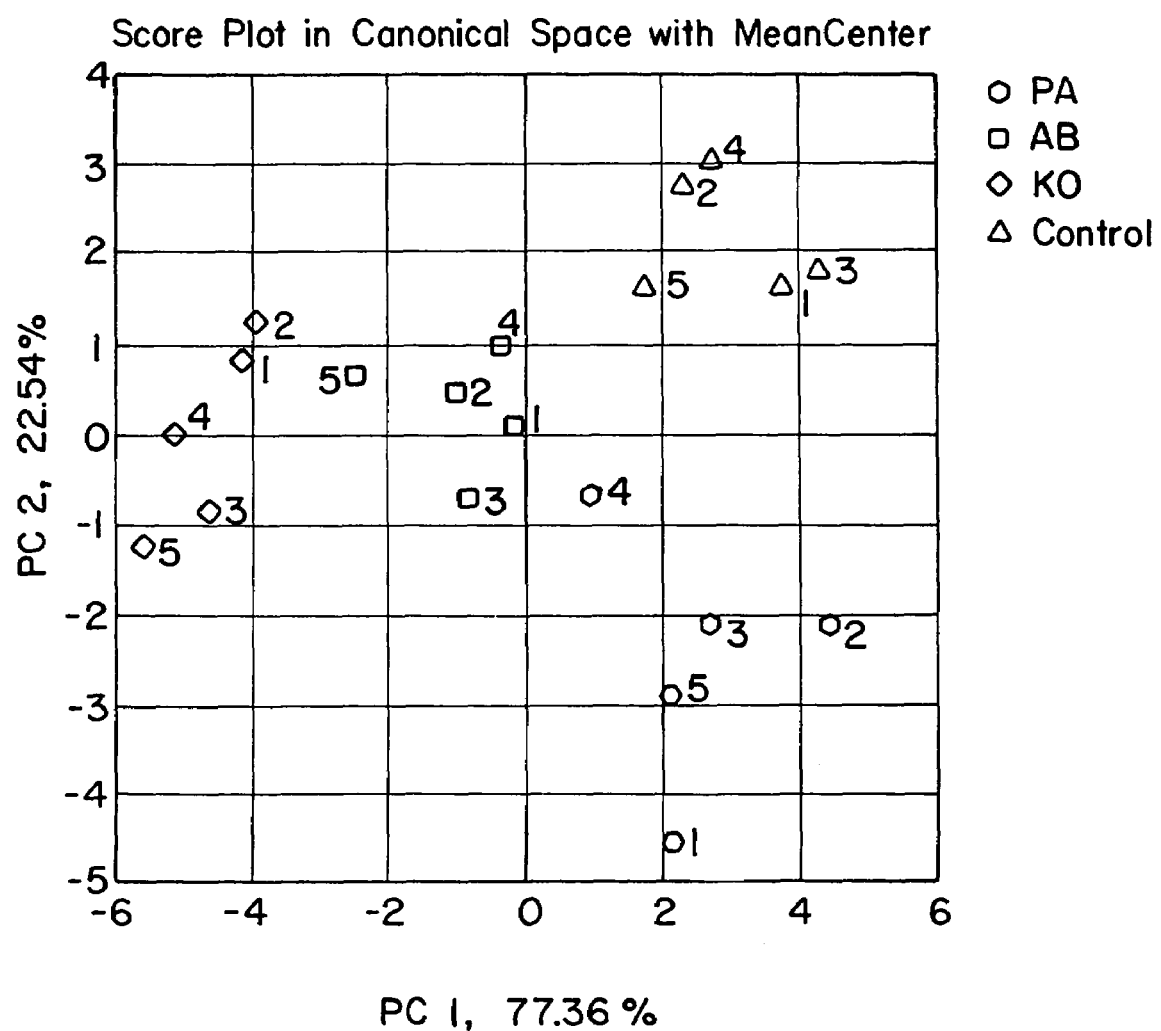
FIG. 1 is a mean-centered canonical projection plot demonstrating the distinction between "smellprints" of different bacteria (*P. aeruginosa, A. baumanii, K. oxytoca*) and controls. PC 1 and PC 2 are Principal Component vectors or factors that show the greatest variance in data. The percents shown are the amount of variance from the whole data set that is captured in that vector.

The term "smellprint" as used herein refers the particular mixture or pattern of odors associated with a particular disease or condition. A smellprint can include marker gases from microorganisms and/or other any other gases resulting from a chemical change produced by the disease process, a physiological condition, the immune system response to a disease or condition, or the response to therapeutic treatment.

The term "in flow communication" as used herein refers to being connected in a manner that allows flow of a substance between two or more regions, areas, etc.

The term "sensor array response profile" as used herein refers to the set of responses from each of the sensors in a particular array.

II. Overview

This invention provides methods and devices for rapid diagnosis of a disease or a condition. In preferred embodiments, the methods and devices comprise contacting an array of sensors with a sample from a mammal suspected of having a disease or condition to generate a sensor array profile, measuring a clinical diagnostic marker for the suspected disease or condition, and then developing a diagnosis using the sensor array profile in combination with the clinical diagnostic marker. The sensor array profile provides a "chemical signature" or "smellprint" of a mammal. If the mammal has a disease or a particular physiological condition, the "smellprint" can include marker gases from microorganisms and/or any other gases resulting from a chemical change produced by the disease process or condition, the immune system response to the disease or condition, or the response to therapeutic treatment. The measured clinical diagnostic marker can be any marker commonly accepted as one that is indicative of a disease. Such markers include by way of example, serology markers (such as leukocyte and erythrocyte count), Clinical Pulmonary Infection Score (CPIS), temperature, secretion amount and character, radiography, respiratory function, and microbiological culture. Those of skill in the art will know of other clinical diagnostic markers that are suitable for the diagnosis of specific physiological conditions or diseases.

In preferred embodiments, the sensor array response profile is generated prior to measuring the clinical diagnostic markers. If analysis of a particular sensor array profile suggests that a patient has a particular disease or condition, then clinical diagnostic markers can be measured to confirm the diagnosis. In other embodiments, the sensor array response profile is generated concurrently with measuring the clinical diagnostic marker. In other embodiments, the sensor array response profile is generated subsequently to measuring the clinical diagnostic markers. In preferred instances the analysis of the sensor array response profile can be used to confirm diagnosis by the clinical diagnostic markers. In certain embodiments, the sensor array profile is analyzed to identify the marker gases in the sample. Marker gases are indicative of certain infections, disorders and medical conditions.

In other aspects, this invention provides methods and devices for monitoring the progression of a disease or condition in a patient, monitoring the effectiveness of treatment over time, and ensuring that the patient does not develop a particular disease or condition. Advantageously, rapid diagnosis allows monitoring in real time, which is not possible with diagnosis via traditional clinical diagnostic markers. In certain embodiments, the method comprises using a sensor array to measure an initial or baseline state, measuring a change with time from the initial or baseline state, monitoring a course of treatment against a disease state, and measuring the return to or toward the initial or baseline state after administration of therapy.

In other aspects, the invention provides a method for determining whether a mammal has a disease or condition and for determining the severity of a disease or condition by comparing the sensor array response profiles from a healthy subject with one from a subject suspected of having a disease or condition. In certain embodiments, this is done without identifying the marker gases in the sample.

It will be apparent to one of skill in the art that combinations of the above methods and devices can be employed.

III. Devices of this Invention

In certain embodiments, the device is a portable, handheld device that a clinician would use when checking on a patient. The sensors in device may be packaged together with the data processing capabilities into a single unit. In other embodiments, the sensors are located to allow for optimal sample collection and are in wired or wireless communication with a base data processing unit located remote from the sensor arrays. In still other embodiments, the sensors are interrogated remotely with a wand/PDA device. The devices used in conjunction with the embodiments of the present invention, may include those described in U.S. Pat. No. 6,244,096, entitled: "Trace level detection of analytes using artificial olfactometry," the disclosure of which is herein incorporated by references in its entirety for all purposes. Furthermore, the method used to obtain a smellprint may include those described in U.S. Pat. No. 6,319,724, entitled: "Trace level detection of analytes using artificial olfactometry," the disclosure of which is herein incorporated by references in its entirety for all purposes.

In certain embodiments, mammalian breath is analyzed from a patient using a ventilator. Preferably, a sensor array is embedded in a ventilator circuit (tubing, filter, or any other attachments used to modify the air inhaled into the ventilator) for either continuous monitoring or monitoring at timed intervals. The sensor array can also be located elsewhere along the fluid stream between the patient lungs and the ventilator pump, or in a separate unit altogether. The data processing capabilities can also be integrated with the sensor array, or the sensor array can be in communication with a base unit which contains the data processing capabilities located elsewhere in the ventilator instrument. In other embodiments, the sensors are polled or interrogated by an external device for readout of response and diagnosis.

In other embodiments, the sensor array is in a closed chamber containing a sample from patient. The sample can be a bodily vapor, fluid, or secretion or any fluid obtained from a mammal. This includes, but is not limited to, breath, breath condensate (i.e., ventilator condensate), urine, perspiration, tears, blood, mucus, pus, saliva, feces, menstruation fluid, sperm, eggs, spinal fluid, mammary gland discharge, or any material collected on a swab. Alternatively, the sensor array is connected to a pump which pulls the vapors from another chamber containing the patient sample. The container holding the material can be a gas sampling bag, vial, or other closed system.

In still other embodiments, the device and methods of the present invention can be adapted and configured to detect within or around various other areas of interest including, but not limited to, mucous membranes, nose, nasal passages, eye, skin, ear, inner ear, mouth, tongue, throat, colon, duodenum, body cavities, stomach, vagina and penis.

Sensor Arrays

Various sensors suitable for detection of marker gases include, but are not limited to: surface acoustic wave (SAW) sensors; quartz crystal microbalance sensors; conductive composites; chemiresistors; metal oxide gas sensors, such as tin oxide gas sensors; organic gas sensors; metal oxide field effect transistor (MOSFET); piezoelectric devices; infrared sensors; temperature sensors, humidity sensors, sintered metal oxide sensors; Pd-gate MOSFET; metal FET structures; metal oxide sensors, such as a Tuguchi gas sensors; phthalocyanine sensors; electrochemical cells; conducting polymer sensors; catalytic gas sensors; organic semiconducting gas sensors; solid electrolyte gas sensors; piezoelectric quartz crystal sensors; dye-impregnated polymer films on fiber optic detectors; polymer-coated micromirrors; electrochemical gas detectors; chemically sensitive field-effect transistors; carbon black-polymer composite chemiresistors; micro-electro-mechanical system devices; micro-opto-electro-mechanical system devices; and Langmuir-Blodgett film sensors.

Preferably, the sensor arrays used in methods of this invention are those described in U.S. Pat. No. 5,571,401, which is incorporated herein by reference. Advantageously, such sensors can be tuned to specific chemical mixtures, are inexpensive and easy to manufacture, and require little power.

Briefly, the sensors described therein are conducting materials and nonconducting materials arranged in a matrix of conducting and nonconducting regions. The nonconductive material can be a nonconducting polymer such as polystyrene. The conductive material can be a conducting polymer, carbon black, an inorganic conductor and the like. The sensor arrays comprise at least two sensors, typically about 32 sensors, and in certain instances 1000 or more sensors up to about $10^6$ sensors. In a preferred embodiment, at least two sensors are compositionally different. The array of sensors can be formed on an integrated circuit using semiconductor technology methods, an example of which is disclosed in PCT Patent Publication No. WO99/08105, entitled "Techniques and Systems for Analyte Detection," published Feb. 19, 1999, and incorporate herein by reference. Another preferred sensor system is disclosed in PCT Patent Publication No. WO99/27357, published Jun. 6, 1999.

In certain embodiments, the temporal response of each sensor (response as a function of time) is recorded and can be displayed. Various responses include, but are not limited to, resistance, impedance, capacitance, inductance, magnetic, optical, etc. The temporal response of each sensor can be normalized to a maximum percent increase and percent decrease that produces a response pattern associated with the exposure of the analyte. By iterative profiling of known analytes, a structure-function database correlating analytes and response profiles is generated. Unknown analytes can then be characterized or identified using response pattern comparison and recognition algorithms. Accordingly, analyte detection systems comprising sensor arrays, a measuring device for detecting responses across each sensor, a computer, a display, a data structure of sensor array response profiles, and a comparison algorithm(s) or comparison tables are provided. In another embodiment, the electrical measuring device or detector is an integrated circuit comprising neural network-based hardware and a digital-analog converter (DAC) multiplexed to each sensor, or a plurality of DACs, each connected to different sensor(s).

In certain embodiments, a method for using the sensors for detecting the presence of an analyte in a fluid involves sensing the presence of marker gas with a chemical sensor comprising first and second conductive leads electrically coupled to and separated by a chemically sensitive sensor as described above by measuring a first response between the conductive leads when the sensor is contacted with a first marker gas at a first concentration and a second different response when the sensor is contacted with a second sample of marker gas at a second different concentration. As discussed above, suitable responses include, but are not limited to, resistance, impedance, capacitance, inductance, magnetic, optical, etc.

Preferably, the sensor arrays will be in a handheld, battery-operated form. The sensor arrays can either be encased in device solely designed to detect and analyze the "smellprint" or part of a small wireless sensing units that can be incorporated into existing portable or disposable medical diagnostic instruments.

IV. Medical Applications of Methods of this Invention

The methods of the present invention have numerous medical applications. In particular, the methods and devices of the present invention are very effective for the detection and diagnosis of both infective and non-infective diseases or conditions. In certain embodiments, they are useful for detection of viral infections, fungal infections, and any other infective agents or causes. The disease can be a lower respiratory tract infection, such as pneumonia, ventilator-associated pneumonia, or bronchitis. The disease can also be an upper respiratory tract infection, such as sinusitis, pharyngitis, or otitis media.

Other medical applications include the detection and treatment monitoring of several pulmonary disease states using the an electronic nose, such as for example, the Cyranose™ 320 in conjunction with other ongoing routine and non-routine clinical procedures. The disease states include asthma, Primary Pulmonary Hypertension (PPH), Chronic Obstructive Pulmonary Disease (COPD), Acute Respiratory Distress Syndrome (ARDS), Cystic Fibrosis (CF), Idiopathic Pulmonary Fibrosis (IPF), Lymphangioleiomyomatosis (LAM), lung cancer, lung transplant, sepsis, Tuberculosis or *Mycobacterium tuberculosis* (TB) as well as pulmonary Tuberculosis, Upper Respiratory Tract Infection (URI), or pneumonia. Other medical applications include the detection and monitoring of diabetes, hypoglycemia, hyperglycemia and nutrition monitoring. Analysis includes analyzing the breath, breath condensate, sputum, pleural fluid or any other material deemed relevant by the clinician.

The disease can be detected by identifying certain "chemical signatures" or "smellprints". These "smellprints" can be a mixture of marker gases from pathogens and off-gases resulting from chemical changes produced by the disease process or condition, the immune system response to a disease or condition, or from the response to therapeutic treatment.

A. Identification of Marker Gases

Alternatively, the disease is diagnosed by identifying marker gases from a particular microorganism or pathogen. In general, certain volatile marker gas(es) characterize the detection or diagnosis of a disease state or medical condition. The marker gases can be off-gases of microorganisms, such as virus, fungus, and a bacterium.

As explained above, volatile sulfur compounds (e.g., $H_2S$, $CH_3$—SH, $CH_3$—S—$CH_3$) are the marker gases implicated in halitosis and periodontal diseases (see, Tonzetich, Arch.Oral Biol., 16:587-597 (1971); Rizzo, Periodontics, 5:233-236 (1967)). Other analytes that have been shown to correlate with such clinical findings include, but are not limited to, volatile organic acids (VOA), indole/skatole (indole), and diamines (see, Goldberg et al, J. Dent. Res., 73:1168-1172 (1994); Goldberg et al., In Rosesberg M Bad Breath Research Perspectives, Ramat Publishing, Tel Aviv, pp. 71-85 (1995)).

In addition, several other analytes have been reported to be associated with oral infections including pyridines/picolines (see, Kostelc et al., J Periodont. Res., 15:185-192 (1981); Kostelc et al., Clin. Chem., 27:842-845 (1981)). Overall, more than 80 volatile compounds have been shown to be associated with saliva or tongue scrapings (see, Claus et al., J High ResoL Chromatogr., 20:94-98 (1997)) and the methods and apparatus of the present invention can be used to advantageously detect such marker compounds and gases.

Using the methods and apparatus of the present invention it is also possible to detect the off-gases associated with bacteria associated with oral maladies including, but not limited to, *Prevotella intermedia; Fusobacterium nucleatum; Porphyromonas gingivalis; Porphyromonas endodontalis; Prevotella loescheii; Hemophilus parainfluenzae; Stomatococcus muci; Treponema denticola*; Veillonella species; *Peptostreptococcus anaerobius; Micros prevotii; Eubacterium limosum; Centipeda periodontii; Selemonad aremidis*; Eubacterium species; Bacteriodes species; *Fusobacterium periodonticum; Prevotella melaninogenica; Klebsiella pneumoniae; Enterobacter cloacae*; Citrobacter species and *Stomatococcus mucilaginus*.

Moreover, a wide variety of analytes and fluids can be detected and analyzed using the disclosed sensors arrays and electronic noses so long as the subject analyte(s) and fluids are capable of generating a differential response across a plurality of sensors of the array. Analyte applications include broad ranges of chemical classes including, but not limited to, organics such as alkanes, alkenes, alkynes, dienes, alicyclic hydrocarbons, arenes, alcohols, ethers, ketones, aldehydes, carbonyls, carbanions, polynuclear aromatics and derivatives of such organics, e.g., halide derivatives, etc.; biomolecules such as sugars, isoprenes and isoprenoids; VOC; VOA; indoles; skatoles; diamines; pyridines; picolines; fatty acids; and derivatives of the foregoing, etc.

B. Methods for Monitoring Disease

In certain embodiments, the sensor array response profiles are stored and used to provide periodic monitoring of the progression of the patent's disease or condition, the patient's response to treatment, or the development of a disease or condition. The sensor array response profiles of this invention are analyzed to identify "smellprints" associated with particular disease. If a "smellprint" associated with a particular disease or a "smellprint" indicating increasing severity of a disease or condition is identified, then the appropriate medical personnel is notified, i.e., nurse or doctor. The medical personnel can then modify treatment or conduct clinical tests to verify the diagnosis. In certain embodiments, the "smellprint" can be compared to a baseline "smellprint" of the individual in a healthy state. Significant deviations from baseline will trigger an appropriate response. For example, methods and apparatus similar to those described in U.S. Pat. App. No. 20021/0037070 A1 ("Cranley"), which is herein incorporated by reference, can be used.

The data may be collected by a patient at home, stored, and processed in the device itself, on a portable computer-readable file, or at a remote location, where it can be electronically transmitted to a physician for evaluation. The data can be stored and transmitted using systems described in WO01/33212, which is herein incorporated by reference.

The conditions monitored by methods of this invention include, but are not limited to, the progression and/or regression of a disease state, bacterial infections, viral, fungal or parasitic infections, the effectiveness of a course of treatment and the progress of a healing process.

In certain instances, the patient is in a nursing home, primary residence or hospital. The patient uses a sensor array device to capture data on an analyte such as, but not limited to, a breath sample, which the patient provides. The data on the breath sample can be optionally transmitted over the Internet or intranet to a processor and then be subsequently analyzed or read by a medical professional at a health company, doctor's office or hospital. Thereafter, the patient can access the diagnostic information on a private Web site for further instructions and treatment. Using the methods of the present invention, real time home health management is realized.

EXAMPLES

The following examples are offered to illustrate, but not to limit, the claimed invention.

Example 1

This example illustrates that an electronic sensor array can be used to distinguish bacterial cultures and to distinguish infected from noninfected patients.

In Vitro Results for Upper Respiratory Bacteria: Identification of Signature Responses This example demonstrates the use of sensor arrays in accordance with embodiments of the present invention for detection of respiratory bacterial pathogens in vitro. This set of experiments was designed to test whether very small quantities of bacteria, collected on fine swabs in vitro, can be discriminated with the electronic nose.

Specifically, the electronic nose's ability to distinguish between swabs containing bacterial cells ("positive") and control swabs without bacterial cells ("negative"), using known plated bacteria was examined. In the first experiment, five swabs of each bacterial species were compared to five control swabbings placed in normal saline. For each of the three bacteria tested, the electronic nose was able to distinguish between the control and bacteria, with a MD between 4.3 and 7.9 (FIG. 1). After selecting out only the most responsive sensors, the MD increased to between 5.4 and 10.0, making it possible for the nose to identify unknowns. The term "MD" refers to the Mahalanobis distance which is a statistical measure of the distance between the centroids of two clusters. A larger MD value signifies a greater degree of separation and therefore greater discrimination of bacterial species by the electronic nose.

In Vivo Results for Rhinosinusitis: Identifying Infected Patients

Figure 3:
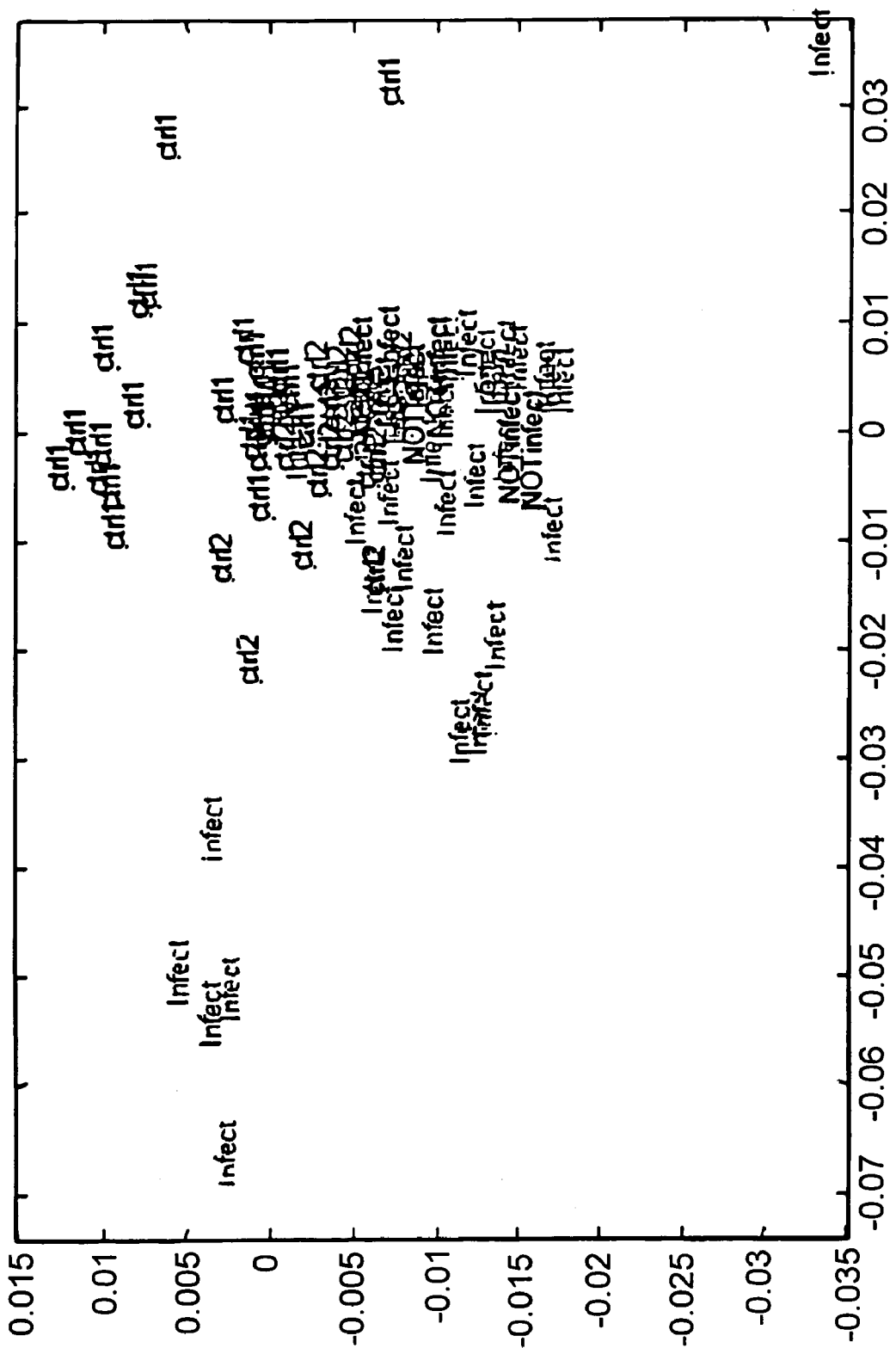
FIG. 3 is a principal component analysis plot of data from patients suspected of having bacterial rhinosinusitis (black=saline alone, red=saline plus blank swabs, green=infected patients, purple=non-infected patients). The X-axis and Y-axis are Principal Component vectors that show the greatest variance in data. Identification of infected vs. not infected samples was obtained from a bacterial culture of a duplicate swab sample.

The ability of sensor arrays used in methods of this invention to detect bacterial rhinosinusitis is demonstrated by the results shown in FIG. 3. In this experiment, the electronic nose was exposed to swabbings obtained endoscopically from sinus cavities of patients suspected of having bacterial rhinosinusitis. Forty-eight specimens were obtained sequentially over the course of approximately six weeks, and the data was then consolidated into a single PCA graph for purposes of analysis (FIG. 3). There was clearly clustering of data, with the control groups being distinct from the sample groups. Furthermore, the non-infected patients clustered centrally amongst a larger grouping of infected patients. It appears that the headspace of swabbings collected from infected patients presents a greater variety of chemical vapors, or greater variation in concentration of chemical vapors, than the non-infected swabs. This difference can serve as a basis for identifying which patients require follow up clinical testing.

Figure 4:
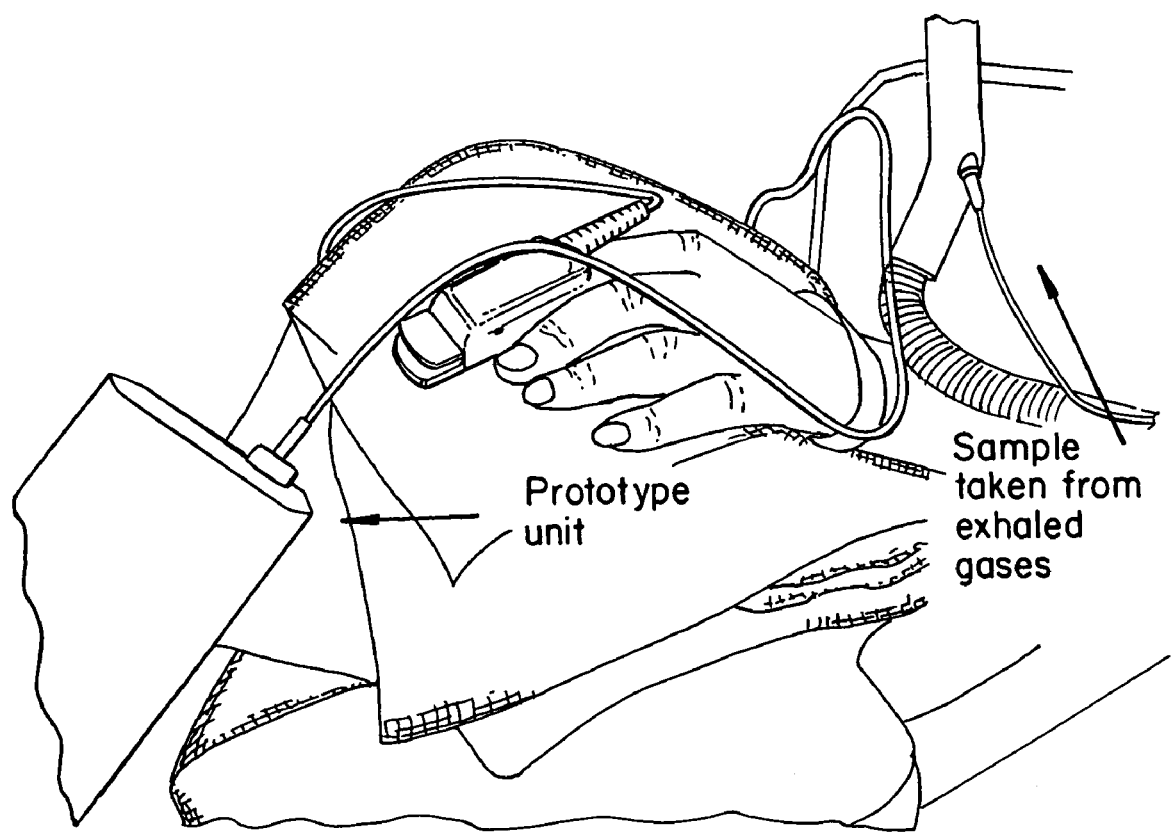
FIG. 4 illustrates a prototype unit of an electronic nose useful for detecting bacterial "smellprints" connected to a ventilator exhaust stream in order to sample exhaled gases from the patient.

In Vivo Results for Ventilator Associated Pneumonia: Identification of Infected Patients The electronic nose was also used to measure 8 mechanically-ventilated patients suspected of ventilator associated pneumonia (VAP) bacterial lung infection. Data were collected by sampling gases directly from the patient's exhaled air with the electronic nose as shown in FIG. 4. Each patient was assigned a CPIS score by the attending physician.

Figure 5:
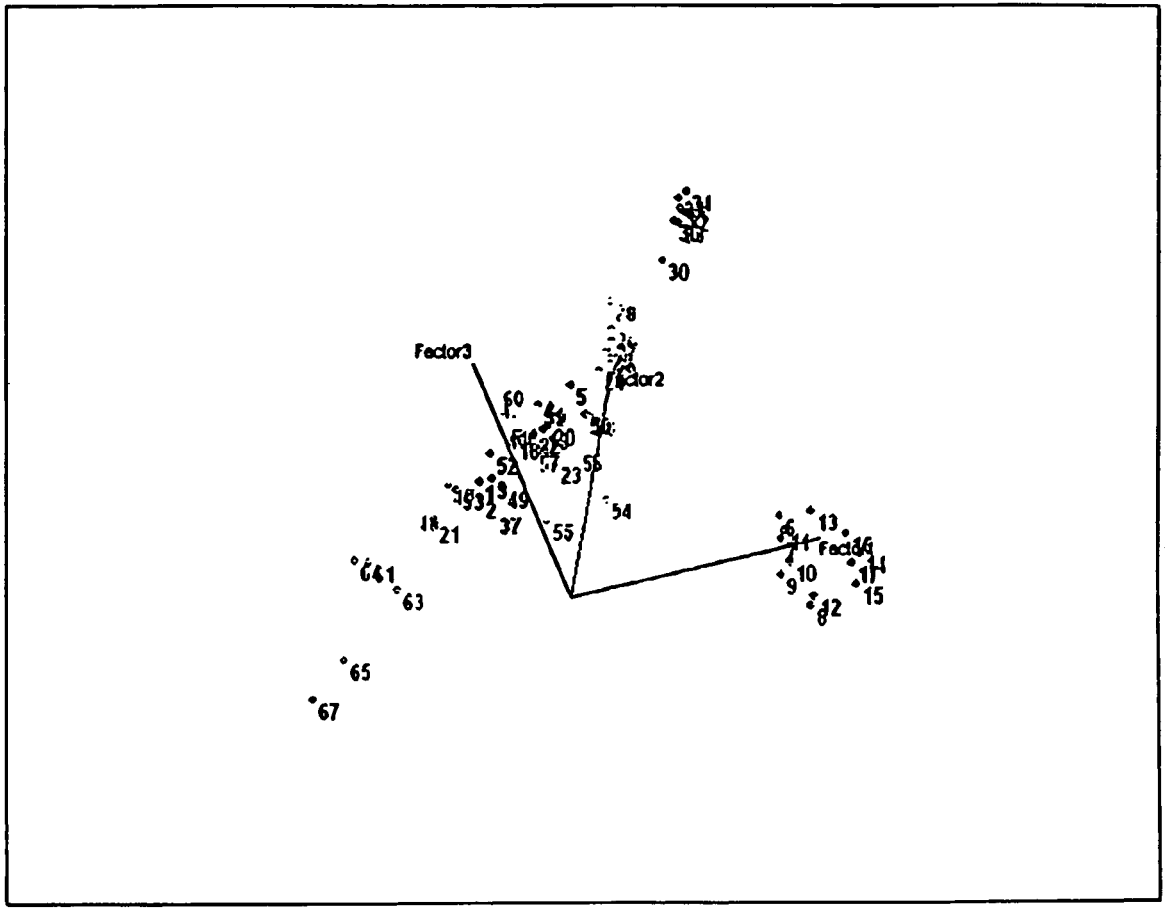
FIG. 5 is a Principal Component Projection Plot demonstrating the discrimination of severely infected patients (red circles=high score) and moderately infected patients (orange circles=medium score) from the control sample (blue circles). Patients with negligible infection (green circle=low score) were not discriminated from the control samples. 5-7 points were measured for each patient. The Factor 1, Factor 2 and Factor 2 axis are Principal Component vectors that show the greatest variance in data.

The PCA plot of the results from the initial eight patient study is shown in FIG. 5. Of the patients, 4 were seriously infected (high score), one was moderately infected (medium score), and three had negligible or no infection (low score). Water was used as a control. The PCA plot shows that the moderately and severely infected patients were all clearly distinguished from the control (red and orange points compared to blue) and the uninfected patients (green points) by the electronic nose. In addition, both the moderately and severely infected patient groups are separated clearly from the control group. Finally, as seen in FIG. 5, the moderately infected patient sample lies "closer" to the control cluster than the severely infected patient samples.

The data, analyzed by PCA, show that the electronic nose is able to distinguish between infected and uninfected patients. This finding suggests that it is possible to train the Cyrano prototype to recognize the "smellprint" of uninfected patients using the control (water). The infected state, and possibly the severity of infection, then could be predicted by distance away from the uninfected (trained) state.

Example 2

Identification of Upper Respiratory Bacteria

This example illustrates the ability of the device used in methods of this invention to identify bacterial cultures.

Figure 2:
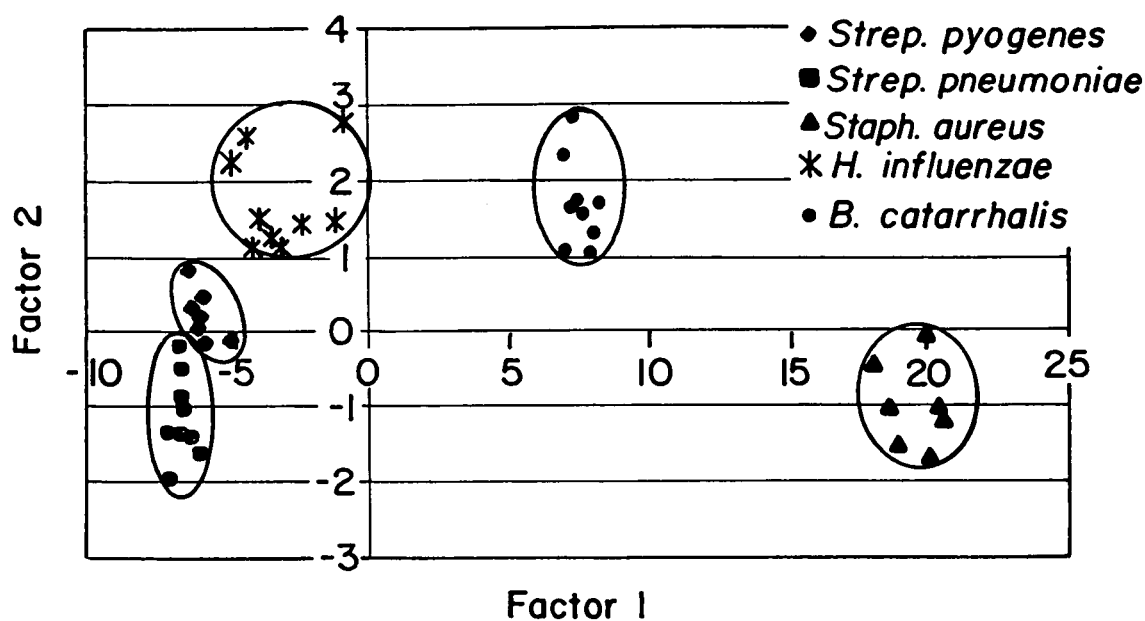
FIG. 2 illustrates the canonical discriminant scores of the principal bacteria responsible for upper respiratory infection (URI) in 24 hour cultures. There is distinct clustering of bacteria by species.

Pure cultures of the most common URI pathogens (*Streptococcus pneumoniae, Streptococcus pyogenes, Staphylococcus aureus, Moraxella catarrhalis, Haemophilus influenzae*) were presented to the sensor array along with uninoculated medium controls. Representative results are shown in FIG. 2. The in vitro results show distinct clustering by species or genus and demonstrate that the sensor array can detect unique chemistries in the air above growing cultures. The patterns of response to these chemical differences are stored as digital "smellprints". Training the devices on pure cultures allows for identification of unknown cultures that are presented for analysis. Over a two-week period, the device correctly identified bacteria with a 93% to 100% correct success rate after a single training session on the first day.

Example 3

Correlation between Clinical Indicator and Sensor Results

This example illustrates that there is a close correspondence between the CPIS score for detection of ventilator-associated pneumonia and the degree of infection predicted from the sensor arrays used in methods of this invention.

Figure 6:
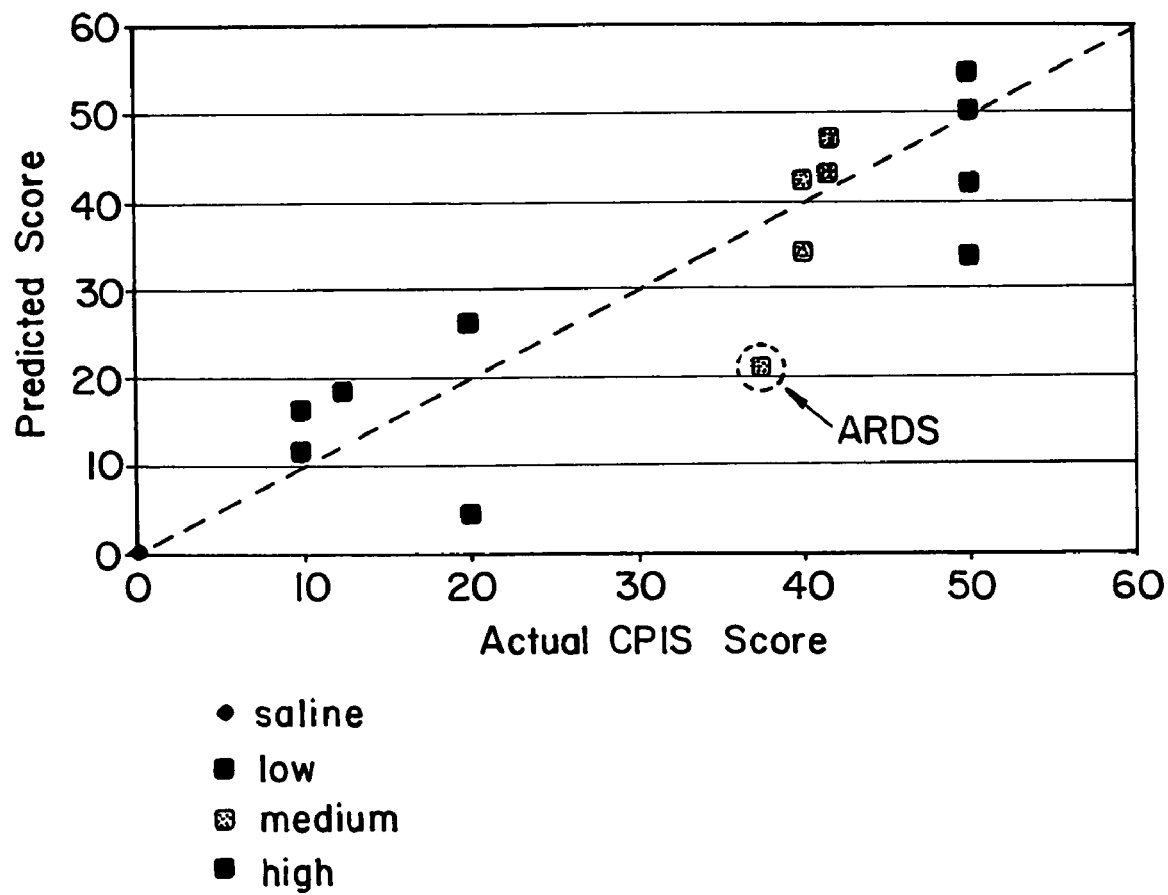
FIG. 6 illustrates the correlation of the predicted and actual pneumonia score for the ventilator patients determined using the Cyrano medical nose prototype. The diagonal line has unit slope. Patients with medium to high score would be treated for infection while patients with low score would not.

Air is sampled directly from the ventilator circuit of patients and the response from the sensor array is compared to clinical indicators of infection. The combined pulmonary infection score (CPIS) incorporates patient temperature, leukocyte count, radiography and several other measures to estimate the risk for pneumonia. Data for 15 patients is shown in FIG. 6. FIG. 6 illustrates the correlation of the predicted and actual pneumonia score for the ventilator patients determined using the Cyrano medical nose prototype. The diagonal line has unit slope. Patients with medium to high score would be treated for infection while patients with low score would not. This figures shows that the predicted scores using an electronic nose correlate well with actual CPIS scores.

Example 4

Device for Diagnosing Ventilator-Associated Pneumonia (VAP)

This example illustrates the use of a portable or hand-held sensing device to detect ventilator associated pneumonia or to aid in the clinical diagnosis.

FIG. 4 shows the device and the ventilator circuit near a patient's mouth. The y-connector near the mouth separates the inhaled and exhaled gas. The inlet of the sensing device is attached to the exhaled gas port on the y connector as indicated by the red arrow. A patient sample is drawn over the sensors by a pump included in the device, or by flow from the ventilator circuit.

Figure 7:
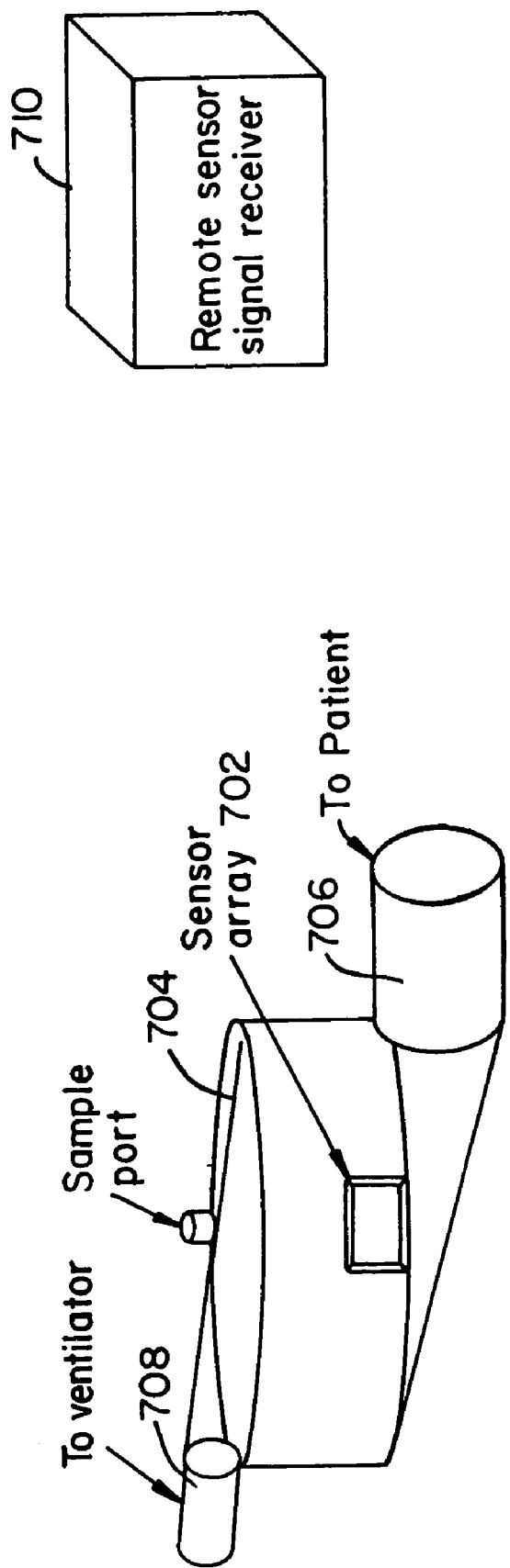
FIG. 7 illustrates a schematic of how a sensor chip can be incorporated into the ventilator circuit.

FIG. 7 shows the detail of how a sensor chip can be incorporated into the ventilator circuit. FIG. 7 shows a sensor array 702 placed in a ventilator chamber 704. The chamber 704 is in fluid communication with the fluid passage extending to the patient 706, and fluid passages extending to the ventilator 708. As is shown in FIG. 7, the processing circuitry 710 for the electronic nose is separately located from the sensor array 702.

Example 5

Device for Diagnosing Rhinosinuitis

This example illustrates the use of a portable sensing device to aid in the clinical diagnosis of rhinosinusitis.

Figure 8:
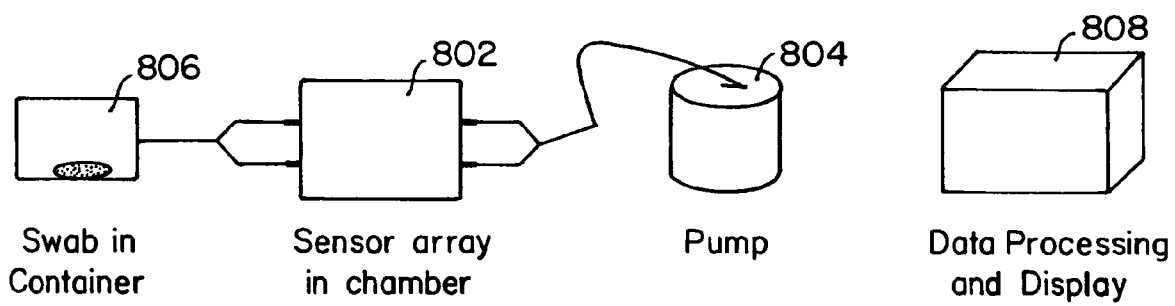
FIG. 8 illustrates a schematic of a portable sensing device to aid in the clinical diagnosis of a physiological condition.

FIG. 8 is a schematic diagram of an embodiment of a system that may be configured to practice the embodiments of the present invention. FIG. 8 shows a sensor array in a closed chamber 802 connected to pump 804 which pulls the vapors from a swab in a container 806 over the sensor array. The container holding the swab is a gas sampling bag, vial, or other closed system. The container with patient sample is disposable and can be removed after each use. The data processing capabilities 808 can either be included in a package with the sensor array and pump or may be at a remote location.

In certain instances, the device is calibrated with a vial of water. In other instances, the sensors are standardized during the manufacturing process.

Once a patient sample has been taken, the data from the patient is immediately analyzed and output identification displayed. Sample identification is designed to correlate with the current clinical methods.

After the identification is made, the clinician is responsible for further decision making. The device is used to monitor the course of treatment if an infection is detected and to monitor patients with chronic sinusitis not caused by bacteria, to verify that no sinus infection has developed.

It is also understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference for all purposes in their entirety.

What is claimed is:

1. A method for determining whether a mammal has a disease, said method comprising:
   (a) contacting an array of sensors with a sample from a mammal suspected of having a disease to generate a first sensor array response profile; and
   (b) comparing said first sensor array response profile with a sensor array profile from a health mammal, thereby determining whether said mammal suspected of having a disease actually has said disease,
   wherein the array of sensors includes a chemical sensor electrically coupled to first and second conductive leads, and
   wherein the contacting step comprises:
      a1) measuring a first response between the first and second conductive leads when the chemical sensor is contacted with a first marker gas at a first concentration; and
      a2) measuring a second response between the first and second conductive leads when the chemical sensor is contacted with the first marker gas at a second concentration different from the first concentration; and
      a3) generating the sensor array response profile based on the first and second responses.

2. The method of claim 1, wherein the first and second responses are responses obtained from the array of sensors that are measured by changes in magnetic or optical characteristics of the array of sensors.

3. A method for determining whether a mammal has a disease, said method comprising:
   (a) contacting an array of sensors with a sample from a first plurality of mammals suspected of having a disease to generate a first sensor array response profile;
   (b) contacting the array of sensors with a sample from a second plurality of mammals not suspected of having a disease to generate a second sensor array response profile; and
   (c) contacting the array of sensors with a sample from the mammal for which a determination is to be made as to whether or not the mammal has the disease, to generate a third sensor array profile;
   (d) evaluating the difference between the first and second sensor array profiles with respect to the third sensor array profile, respectively, thereby determining whether not the mammal has the disease,
   wherein the array of sensors includes a chemical sensor electrically coupled to first and second conductive leads, and
   wherein the contacting step comprises:
      a1) measuring a first response between the first and second conductive leads when the chemical sensor is contacted with a first marker gas at a first concentration; and
      a2) measuring a second response between the first and second conductive leads when the chemical sensor is contacted with the first marker gas at a second concentration different from the first concentration; and
      a3) generating the first and second sensor array response profit s based on the first and second responses.

4. The method of claim 3, where in the array of sensors includes a chemical sensor electrically coupled to first and second conductive leads, and wherein each of the contacting steps comprises:
- a1) measuring a first response between the first and second conductive leads when the chemical sensor is contacted with a first marker gas at a first concentration; and
- a2) measuring a second response between the first and second conductive leads when the chemical sensor is contacted with the first marker gas at a second concentration different from the first concentration; and
- a3) generating the respective first and second sensor array response profiles based on die first and second responses.

5. The method of claim 3, wherein the first and second responses are responses obtained from the array of sensors that are measured by changes in magnetic or optical characteristics of the array of sensors.

6. A method for detecting a physiological condition in a mammal, said method comprising:
- (a) contacting an array of sensors with a sample from a first mammal suspected of having a physiological condition to generate a baseline sensor array response profile;
- (b) measuring a clinical diagnostic marker for said physiological condition; and
- (c) determining the severity of the physiological condition using said sensor array response profile in combination with said clinical diagnostic marker;
- (d) contacting the array of sensors with a sample from a second mammal having a disease for a second time to generate a second sensor array response profile;
- (e) measuring said clinical diagnostic marker for said disease for a second time; and
- (f) determining the severity of the disease in said second mammal using said first and second sensor array response profiles in combination with the first and second measurement of said clinical diagnostic marker, thereby monitoring said disease in said second mammal.

7. A method for detecting presence or absence of a physiological condition in a mammal, said method comprising:
- (a) contacting an array of sensors with a sample from a mammal suspected of having a physiological condition to generate a sensor array response profile;
- (b) measuring a clinical diagnostic marker for said physiological condition; and
- (c) developing a diagnosis using said sensor array response profile in combination wit said clinical diagnostic marker, thereby detecting the presence or absence of said physiological condition in said mammal, wherein the array of sensors includes a chemical sensor electrically coupled to first and second conductive leads, and wherein the contacting step comprises:
- a1) measuring a first response between the first and second conductive leads when the chemical sensor is contacted with a first marker gas at a first concentration; and
- a2) measuring a second response between the first and second conductive leads when the chemical sensor is contacted with the first marker gas at a second concentration different from the first concentration; and
- a3) generating the sensor array response profile based on the first and second responses.

8. The method of claim 7, wherein the first and second responses are responses obtained from the array of sensors that are measured by changes in magnetic or optical characteristics of the array of sensors.

* * * * *